(12) United States Patent
Sehgal

(10) Patent No.: US 8,431,334 B2
(45) Date of Patent: *Apr. 30, 2013

(54) METHOD FOR REMOVING ANTIPLATELET AGENT AND ANTICOAGULANT FROM A PLATELET COMPOSITION BY DIAFILTRATION

(75) Inventor: Lakshman R. Sehgal, Monarch Beach, CA (US)

(73) Assignee: Biovec Transfusion, LLC, Chicago, IL (US)

( * ) Notice: Subject to any disclaimer, the term of this patent is extended or adjusted under 35 U.S.C. 154(b) by 236 days.

This patent is subject to a terminal disclaimer.

(21) Appl. No.: 12/955,200

(22) Filed: Nov. 29, 2010

(65) Prior Publication Data
US 2011/0076669 A1 Mar. 31, 2011

Related U.S. Application Data

(63) Continuation-in-part of application No. 11/330,132, filed on Jan. 12, 2006, now Pat. No. 7,694,338, and a continuation-in-part of application No. 12/792,259, filed on Jun. 2, 2010.

(60) Provisional application No. 61/282,306, filed on Jan. 19, 2010, provisional application No. 61/187,052, filed on Jun. 15, 2009.

(51) Int. Cl.
*A01N 1/02* (2006.01)

(52) U.S. Cl.
USPC ............................................................ 435/2

(58) Field of Classification Search .................. None
See application file for complete search history.

(56) References Cited

U.S. PATENT DOCUMENTS

| | | | |
|---|---|---|---|
| 4,455,299 A | 6/1984 | Grode | |
| 4,800,016 A | 1/1989 | Yang | |
| 5,256,559 A | 10/1993 | Maraganore et al. | |
| 5,798,238 A | 8/1998 | Goodrich, Jr. et al. | |
| 5,801,063 A | 9/1998 | Grandics et al. | |
| 5,858,238 A | 1/1999 | McRea et al. | |
| 5,869,701 A | 2/1999 | Park et al. | |
| 5,919,614 A | 7/1999 | Livesey et al. | |
| 5,955,256 A | 9/1999 | Sowemimo-Coker et al. | |
| 5,981,163 A | 11/1999 | Horowitz et al. | |
| 6,030,767 A | 2/2000 | Wagner et al. | |
| 6,087,141 A | 7/2000 | Margolis-Nunno et al. | |
| 6,106,773 A | 8/2000 | Miekka et al. | |
| 6,733,471 B1 | 5/2004 | Ericson et al. | |
| 6,833,236 B1 | 12/2004 | Stienstra | |
| 2001/0044584 A1 | 11/2001 | Kensey | |
| 2004/0223957 A1 | 11/2004 | Lucas et al. | |
| 2006/0177811 A1 * | 8/2006 | Sehgal et al. ................ 435/2 |
| 2008/0138791 A1 | 6/2008 | Hoffmeister et al. | |
| 2010/0221697 A1 | 9/2010 | Sehgal | |

FOREIGN PATENT DOCUMENTS
WO    WO 99/55346   * 11/1999

OTHER PUBLICATIONS

International Search Report, mailed Dec. 29, 2011 (International Application No. PCT/US2011/025432, filed Feb. 18, 2011).
Written Opinion of the International Search Authority, mailed Dec. 29, 2011 (International Application No. PCT/US2011/025432, filed Feb. 18, 2011).
International Search Report (International Application No. PCT/US2010/037203, filed Jun. 3, 2010).
Written Opinion of the International Search Authority (International Application No. PCT/US2010/037203, filed Jun. 3, 2010).
Warnhol TZ, Ascan, et ai., "Vasoactive Role of the aVβ3 iNtegrin in Rabbit Carotid Artery: Endothelium-Dependent and Independent Effects", American Heart Association, 71st Scientific Sessions, Nov. 8-11, 1998.
Mousa, Shaker A., et al., "Comparison of the Effect of Different Platelet GPIIb/IIa Antagonists on the Dynamics of 2 Platelet/Fibrin-Mediated Clot Strength Induced Using Thromboelastography", Thrombosis Research, Jul. 3, 2001, 0 vol. 104, pp. 49-56.
Bode et al., "Extended Storage of Platelets in an Artificial Medium with the Platelet Activation Inhibitors Prostaglandin E1 and Theophylline", Vox Sang. 60 : 105-112 (1991).
Mousa et al. "Antiplatelet and Antithrombotic Efficacy of DMP 728, a Novel Platelet GPIIb/IIIa Receptor Antagonist", Circulation 89 (1) : 3-12 (1994).
Frietsch et al. "Artificial oxygen carriers", European Journal of Anasthesiology 15 : 571-584 (1998).
Lowe, "Second-Generation Perfluorocarbon Emulsion Blood Substitutes", Art. Cells, Blood Subs. and Immob. Biotech. 28 (1) : 25-38 (2000).
Uzan , "Antithrombotic agents", Chapter 12, Emerging Drugs 3: 189-208 (1998).
American Heritage Stedman's Medical Dictionary 2002, definition of "cell culture", accessed Sep. 8, 2008.
Hirsh, J. et al., "New antithrombotic agents", The Lancet, vol. 353, pp. 1431-1436, Apr. 24, 1999.
Pinto, Donald J.P. et al., "Discovery of 1-[3-(Aminomethyl)phenyl]-N-[3-fluoro-2'-(methylsulfony1)-[1 ,1'-biphenyl]-4-yl]-3-{trifluoromethyl)-1 H-pyrazole-5-carboxamide (DPC423), a Highly Potent, Selective, and Orally Bioavailable Inhibitor of Blood Coagulation Factor Xa1", J. Med. Chem., vol. 44, pp. 566-578, (2001).
Pruitt, James R et al., "Isoxazolines and Isoxazoles as Factor Xa Inhibitors", Bioorg. Med. Chem. Lett., vol. 10, pp. 685-689, (2000).
Quan, Mimi L. et al., "Design and Synthesis of Isoxazoline Derivatives as Factor Xa Inhibitors", J. Med. Chem., vol. 42, pp. 2752-2759, (1999).

(Continued)

*Primary Examiner* — Sandra Saucier
(74) *Attorney, Agent, or Firm* — Ping Wang; Andrews Kurth LLP

(57) ABSTRACT

The present invention relates to methods for preserving platelet. In one embodiment, the method includes the steps of mixing platelets with a platelet preservation composition to form a platelet preparation, storing the platelet preparation for a desired period of time, and removing the antiplatelet agent and the anticoagulant from the platelet preparation by diafiltration prior to transfusion of the platelets. The platelet preservation composition comprises an effective amount of an antiplatelet agent and an effective amount of an anticoagulant.

11 Claims, 15 Drawing Sheets
(14 of 15 Drawing Sheet(s) Filed in Color)

OTHER PUBLICATIONS

Sato, K. et al., "Relationship between the antithrombotic effect of YM-75466, a novel factor Xa inhibitor, and coagulation parameters in rats", European Journal of Pharmacology, vol. 347, pp. 231-236, (1998).

Wong, P.C., et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357, (2000).

Fareed, J. et al., "New antithrombotic drugs: A perspective", Current Opinion in Cardiovascular, Pulmonary & Renal Investigational Drugs, vol. 1, No. 1, pp. 40-55, (1999).

Herbert, J.M., et al., "DX 9065A, a Novel, Synthetic, Selective and Orally Active Inhibitor of Factor Xa: In Vitro and In Vivo Studies", The Journal of Pharmacology and Experimental Therapeutics, vol. 276, No. 3, pp. 1030-1038, (1996).

Nagahara, T. et al., "Design, Synthesis and Biological Activities of Orally Active Coagulation Factor Xa Inhibitors", Eur. J. Med. Chem. vol. 30 (Supplemental), pp. 140s-143s, (1995).

Ewing, W.R., et al., "Progress in the design of inhibitors of coagulation factor Xa", Drugs of the Future, vol. 24, D No. 7, pp. 771-787, (1999).

Al-Obeidi, F., et al., "Factor Xa inhibitors", Exp. Opin. Ther. Patents, vol. 9, No. 7, pp. 931-953, (1999).

Krishnamurti, C., et al., "Reduction of blood loss by infusion of human platelets in a rabbit kidney injury model", Transfusion, vol. 39, pp. 967-974, (Sep. 1999).

Abendschein. D.R . et al., "Effects of ZK-807834, a Novel Inhibitor of Factor Xa, on Arterial and Venous Thrombosis in Rabbits", J. Cardiovasc. Pharmacol., vol. 35, No. 5, pp. 796-805, retrieved Oct. 11, 2006, <http:\\gateway.ut.ovid.com.gwllovidweb.cgi>, May 2000.

Ostrem, JA, et al., "Discovery of a Novel, Potent, and Specific Family of Factor Xa Inhibitors via Combinatorial Chemistry", Biochemistry, vol. 37, No. 4, pp. 1053-1059, 1998.

\* cited by examiner

METHOD FOR REMOVING ANTIPLATELET AGENT AND ANTICOAGULANT FROM A PLATELET COMPOSITION BY DIAFILTRATION

This application is a continuation-in-part of U.S. patent application Ser. No. 11/330,132, filed on Jan. 12, 2006, now U.S. Patent No. 7,964,338, and a continuation-in-part of U.S. patent application Ser. No. 12/792,259, filed on Jun. 2, 2010 and claiming priority of U.S. Provisional Application Ser. No. 61/187,052, filed on Jun. 15, 2009 and U.S. Provisional Application Ser. No. 61/282,306, filed on Jan. 19, 2010. The aforementioned applications are incorporated herein by reference in their entirety.

FIELD

The present invention relates generally to preservation of platelets and, in particular, to methods for storing platelets in a preservation solution containing an antiplatelet agent and an anticoagulant, and removing the antiplatelet agent and the anticoagulant from stored platelets prior to clinical application.

BACKGROUND

When blood vessels are damaged, cell fragments released from the bone marrow, called platelets, adhere to the walls of blood vessels and form clots to prevent blood loss. It is important to have adequate numbers of normally functioning platelets to maintain effective clotting, or coagulation, of the blood. Occasionally, when the body undergoes trauma, or when the platelets are unable to function properly, it is necessary to replace or transfer platelet components of blood into a patient. Most commonly, platelets are obtained from volunteer donors either as a component of a whole blood unit, or via plateletpheresis (withdrawing only platelets from a donor and re-infusing the remaining of the blood back into the donor). The platelets then are transferred to a patient as needed, in a process referred to as "platelet transfusion".

Platelet transfusion is indicated under several different scenarios. For example, an acute blood loss, either during an operation or as a result of trauma, can cause the loss of a large amount of platelets in a short period of time. Platelet transfusion is necessary to restore a normal ability to control blood flow, or haemostasis. In a medical setting, an individual can develop a condition of decreased number of platelets, a condition known as thrombocytopenia. The condition can occur as a result of chemotherapy, and requires platelet transfusion to restore normal blood clotting.

Unlike red blood cells, which can be stored for forty-five (45) days, platelets can be stored for only five to seven days. The short storage term, or shelf-life, of the platelets severely limits the useful span for a platelet supply. A consequence of this short shelf-life is that platelets must be collected close to their time of use, which makes it extremely difficult to coordinate platelet collection and platelet supply.

One reason that platelets have such a short shelf-life is because platelets become activated during the process of collection. The activation process leads to externalization of platelet canalicular surfaces exposing receptor sites, such as GPIIb/IIIa. Phosphatidylserine residues on activated platelets tend to cause platelet aggregation, which results in cell death (i.e., apoptosis) upon re-infusion into patients. Thus, a platelet's functional half-life is significantly reduced.

Another reason that platelets have a short shelf-life is because an inadequate oxygen supply alters the metabolic activity of the platelets. In an environment lacking a sufficient oxygen supply, the platelets undergo an anaerobic mechanism leading to accumulation of lactic acid. The increased concentration of lactic acid causes a drop in pH, and results in cell death. Although platelets can be stored in gas permeable bags using a shaker bath under a stream of air to help overcome this problem, such storage methods are costly and extremely inefficient and inadequate in meeting the oxygen requirements of the stored platelets.

Platelet sterility is difficult to maintain because platelets cannot be stored at low temperatures, for example −80° C. to −40° C. As previously mentioned, a low storage temperature for the platelets initiates an activation process within the platelets that leads to aggregation and cell death. Nonetheless, bacterial growth in the platelet medium at suitable storage temperatures, e.g., room temperature, can lead to an unacceptable occurrence of bacterial contamination in platelets used for transfusion. As a result, the Food and Drug Administration (FDA) limits the storage time of platelets to five days, thereby safeguarding the transfusion supply from bacterial contamination.

SUMMARY

A method for preserving platelets is disclosed. The method contains the steps of mixing platelets with a platelet preservation composition to form a platelet preparation, the platelet preservation solution comprises an effective amount of an antiplatelet agent and an effective amount of an anticoagulant; storing the platelet preparation for a desired period of time; and removing the antiplatelet agent and the anticoagulant from the platelet preparation by diafiltration prior to transfusion of the platelets.

In an embodiment, the removing step comprises: flowing the platelet preparation through a filtering tube comprising a filtering membrane and separating the antiplatelet agent and anticoagulant from the platelet preparation by tangential flow filtration.

In another embodiment, the filter membrane comprises a material selected from the group consisting of regenerated cellulose, cellulose acetate, polyamide, polysulfone, polyethersulfone and combinations thereof.

In another embodiment, the filter membrane comprises polysulfone or polyethersulfone.

In another embodiment, the filter membrane has a pore size ranging from molecular weight cut off of 3000 daltons to 0.5 micron.

In another embodiment, the filtering tube has an inner diameter of at least 0.5 mm.

In another embodiment, the platelet preparation flows through the filtering tube at a flow rate of 150 to 3500 ml/min.

In another embodiment, an extraction liquid is circulated outside the filtering tube in a counter current manner.

In another embodiment, the extraction fluid comprises 0.9% w/v sodium chloride.

In another embodiment, the antiplatelet agent is a GPIIb/IIIa inhibitor and the anticoagulant is a thrombin inhibitor or a factor Xa inhibitor.

In another embodiment, the antiplatelet agent is eptifibatide and the anticoagulant is argatroban.

Also disclosed is a method for preserving platelets. The method comprises mixing platelets with a platelet preservation composition to form a platelet preparation, the platelet preservation composition comprises an effective amount of an antiplatelet agent and an effective amount of an anticoagulant, storing the platelet preparation for a desired period of time, and passing the platelet preparation through a porous material that specifically binds to the antiplatelet agents and anticoagulants to remove the antiplatelet agent and the anticoagulant from the platelet preparation prior to transfusion of the platelets.

In an embodiment, the porous material comprises a nanofiber.

In a related embodiment, the cellulose nanofiber has a diameter between 5-60 nm.

In another related embodiment, the cellulose nanofiber is modified to provide specific binding sites for a given antiplatelet agent or an anticoagulant.

In an embodiment, the porous material comprises a reinforced composite film comprising 90% polyvinyl alcohol and 10% nanofiber.

In a related embodiment, the nanofiber is a biodegradable nanofiber.

In another related embodiment, the biodegradable nanofiber forms a porous filter with a thickness of 200-800 nm, a pore size of 2-30 micron, and a porosity of 94-96%.

BRIEF DESCRIPTION OF FIGURES

The file of this patent contains at least one drawing executed in color. Copies of this patent with color drawings will be provided by the Patent and Trademark Office upon request and payment of the necessary fee.

DETAILED DESCRIPTION

Figure 1:
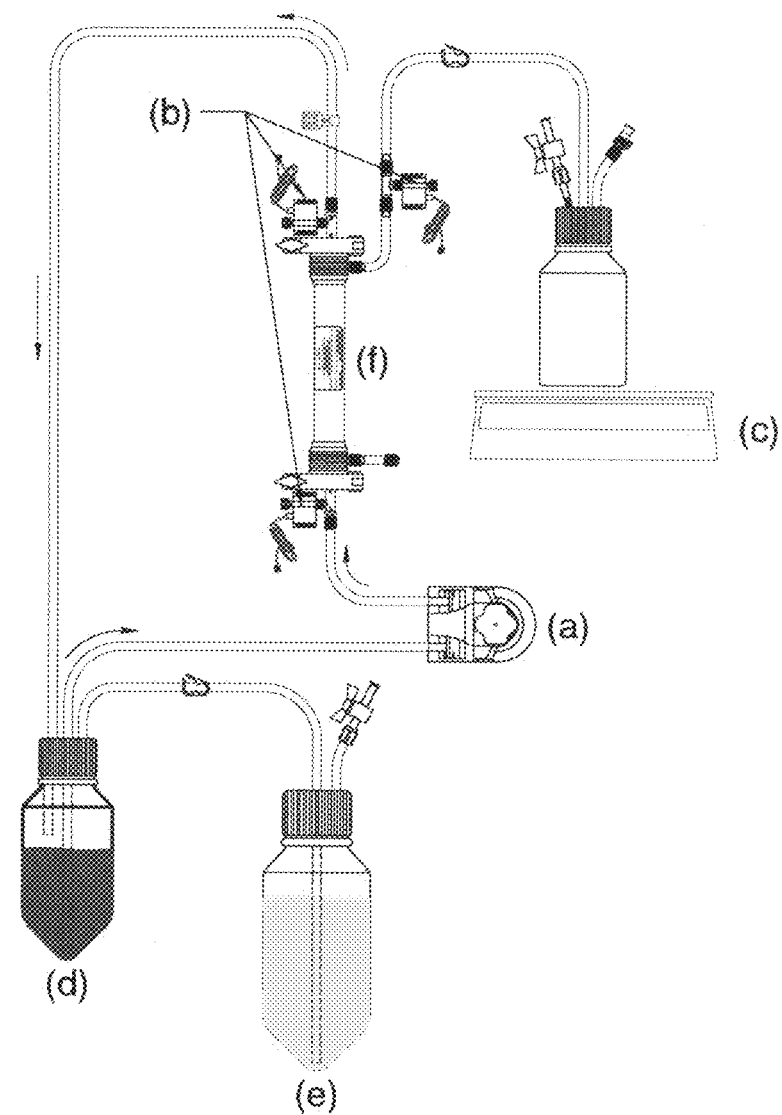
FIG. 1 is a diagram showing a typical continuous diafiltration system.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

One aspect of the present invention relates to a method for preserving platelets. The method comprises the steps of mixing inactivated, functional platelets with a platelet preservation composition containing an effective amount of at least one antiplatelet agent and an effective amount of at least one anticoagulant to form a platelet preparation, storing the platelet preparation for a desired period of time, and removing the antiplatelet agent and the anticoagulant from the platelet preparation prior to transfusion of the platelets.

The Inactivated, Functional Platelets

The inactivated, functional platelets can be in the form of whole blood, a platelet-containing component of whole blood, or isolated platelets substantially free of red blood cells and other blood nutrients.

Typically, the blood is whole blood isolated from a mammal for use in the same species. In the case of a human, the blood is isolated and separated into the three core components of whole blood, i.e., plasma, cells, and platelets. The whole blood, or only the platelet component of the whole blood, can be treated with the preservative composition. If whole blood is treated, a preferred embodiment contemplates the use of only some components of the proposed preservative composition, such as the antiplatelet agent and anticoagulant, for whole blood storage. The blood can then be fractionated and the platelet component can be further mixed with the preservative composition of the present invention for storage.

Functional activities of platelets are determined by their ability to aggregate in the presence of certain biological agents and their morphology. Platelet function also can be assessed by the maintenance of the pH upon limited storage of a solution containing the platelets and in vivo haemostatic effectiveness using the rabbit kidney injury model described by Krishnamurti et al., [*Transfusion*, 39:967 (1999)]. Structural integrity of platelets is assessed by in vivo survival following radiolabeling with carbon-15 or indium-111 and identification of the presence of specific platelet antigens.

The platelets may be isolated from the whole blood using methods commonly used in the art. In one embodiment, a unit of whole blood is centrifuged using settings that precipitate only the cellular components of the blood (e.g., red blood cells and white blood cells). At these settings, the platelets remain suspended in the plasma. The platelet-rich plasma (PRP) is removed from the precipitated blood cells, then centrifuged at a faster setting to harvest the platelets from the plasma.

In another embodiment, the whole blood is centrifuged using settings that cause the platelets to become suspended in the "buffy coat" layer, which includes the platelets and the white blood cells. The "buffy coat" is isolated in a sterile bag, suspended in a small amount of red blood cells and plasma, then centrifuged again to separate the platelets and plasma from the red and white blood cells.

In another embodiment, apheresis platelets are collected using a mechanical device that draws blood from the donor and centrifuges the collected blood to separate out the platelets and other components to be collected. The remaining blood is returned to the donor.

The platelets used in the invention can be sterilized by chemical sterilization, radiation, or a combination thereof, in the presence of the platelet preservation composition. For example, the platelets can be sterilized by chemical filtration; ultraviolet radiation, such as UVA, UVB, and UVC; gamma-radiation; ionizing radiation, such as x-ray radiation; or by using a chemical as a photosensitizer. Methods for sterilizing platelets are well known in the art and include, for example, the methods described in U.S. Pat. Nos. 5,798,238; 5,869,701; 5,955,256; 5,981,163; 6,030,767; 6,087,141; and 6,106,773.

The Platelet Preservation Composition

The platelet preservation composition contains an effective amount of at least one antiplatelet agent and an effective amount of at least one anticoagulant. As used herein, the term "effective amount" refers to a quantity that is capable of achieving an intended effect.

Any agent that reversibly impedes platelet activation and/or aggregation by blocking sites on the platelet surface can be used as the antiplatelet agent in the present invention. As used herein, the term "reversible" or "reversibly" refers to an act, such as binding or associating, that is capable of reverting back to an original condition prior to the act, for example the state of being unbound or disassociated, either with or without the assistance of an additional constituent.

Antiplatelet agents can include, but are not limited to, active agents that bind GPIIb/IIIa sites in a reversible manner, and non-steroidal anti-inflammatory drugs (NSAIDs). Examples of suitable antiplatelet agents for binding GPIIb/IIIa sites in a reversible manner include eptifibatide (INTEGRILIN™, Schering-Plough Corporation, Kenilworth, N.J., U.S.A.), orbofiban, xemilofiban, Lamifiban, tirofiban, abciximab, XJ757, DUP728, XR299, bifunctional inhibitors of both GPIIb/IIIa as described in U.S. Pat. No. 5,242,810, P2Y12 receptor antagonist such as prasugrel, cungrelor and AZD6140, second messenger effectors such as "Thrombosol™" (Life Cell Corp), linear or novel cyclic RGD peptide analogs, cyclic peptides, peptidomimetics and non-peptide analogs conjugated to nitric oxide donor and the like, and mixtures thereof.

In certain embodiments, the antiplatelet agent has short to ultra short half-life. By short-to-ultra short half life is meant that the antiplatelet agent is cleared from circulation within 15 minutes to 8 hours after the infusion of the antiplatelet agent into the patient is stopped.

In one embodiment, the antiplatelet agent is an active agent that binds to or associates with the GPIIb/IIIa sites in a reversible manner and has a circulating half-life of inhibition of 4 hours or less. Short to ultra-short acting GPIIb/IIIa antagonist might include eptifibatide, tirofiban, abciximab (Reopro), lefradafiban, sibrafiban, orbofiban, xemilofiban, lotrafiban, XJ757, and XR299 (Class II). In one embodiment, the antiplatelet agent is eptifibatide. In another embodiment, the antiplatelet agent is eptifibatide at a final concentration of about 5-500 µg per unit of platelet. In another embodiment, the antiplatelet agent is eptifibatide at a final concentration of about 50 µg per unit of platelet.

Non-steroidal anti-inflammatory drugs (NSAIDS) are commonly available, and typically are used for treating inflammation. Generally, NSAIDS can have a salicylate-like or non-salicylate structure. NSAIDS suitable for the invention can be salicylate-like or non-salicylate NSAIDS that bind reversibly and inhibit platelet aggregation in vitro, but are cleared rapidly from the body (typically, in less than about 2 hours). NSAIDS suitable for the invention include, but are not limited to, salicylate-like NSAIDS, such as acetaminophen, carprofen, choline salicylate, magnesium salicylate, salicylamide, sodium salicylate, sodium thiosulfate, and mixtures thereof. Examples of non-salicylate NSAIDS include, but are not limited to, diclofenac sodium, diflunisal, etodolac, fenoprofen calcium, flurbiprofen, hydroxychloroquine, ibuprofen, indomethacin, ketoprofen, ketorolac tromethamine, meclofenamate sodium, mefenamic acid, nabumetone, naproxen, naproxen sodium, oxyphenbutazone, phenylbutazone, piroxicam, sulfinpyrazone, sulindac, tolmetin sodium, dimethyl sulfoxide, and mixtures thereof.

In addition, any agent that inhibits chemical pathways within the platelets leading to reduction in platelet activation is suitable for the invention. Typically, agents that inhibit chemical pathways leading to reduced platelet activation are calcium sequestering agents, such as calcium channel blockers, α-blockers, β-adrenergic blockers and mixtures thereof. More specific examples of calcium sequestering agents include, but are not limited to, anticoagulant citrate dextrose solution, anticoagulant citrate dextrose solution modified, anticoagulant citrate phosphate dextrose solution, anticoagulant sodium citrate solution, anticoagulant citrate phosphate dextrose adenine solution, potassium oxalate, sodium citrate, sodium oxalate, amlodipine, bepridil hydrochloride, diltiazem hydrochloride, felodipine, isradipine, nicardipine hydrochloride, nifedipine, nimodipine, verapamil hydrochloride, doxazocin mesylate, phenoxybenzamine hydrochloride, phentolamine mesylate, prazosin hydrochloride, terazosin hydrochloride, tolazoline hydrochloride, acebutolol hydrochloride, atenolol, betaxolol hydrochloride, bisoprolol fumarate, carteolol hydrochloride, esmolol hydrochloride, indoramine hydrochloride, labetalol hydrochloride, levobunolol hydrochloride, metipranolol hydrochloride, metoprolol tartrate, nadolol, penbutolol sulfate, pindolol, propranolol hydrochloride, terazosin hydrochloride, timolol maleate, guanadrel sulfate, guanethidine monosulfate, metyrosine, reserpine and mixtures thereof.

The amount of the antiplatelet agent present in the platelet preservative composition depends on the type of antiplatelet agent. The amount of antiplatelet agent is sufficient to reversibly inhibit binding to a ligand or a site on the platelet in a manner that is sufficient to inhibit platelet function. For GPIIb/IIIa inhibitors, suitable amounts in the platelet preservation composition are about 0.2 µg/ml to about 20 µg/ml. For NSAIDs, suitable amounts in the platelet preservation composition are about 0.1 mg/ml to about 1 mg/ml.

The anticoagulants include, but are not limited to, heparin, heparin substitutes, prothrombopenic anticoagulants, platelet phosphodiesterase inhibitors, dextrans, thrombin antagonists/inhibitors, and mixtures thereof.

Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; and heparin sodium dihydroergotamine mesylate.

Suitable prothrombopenic anticoagulants include, but are not limited to, anisindione, dicumarol, warfarin sodium, and the like. Examples of phosphodiesterase inhibitors suitable for use in the invention include, but are not limited to, anagrelide, dipyridamole, pentoxifyllin, and theophylline.

Suitable dextrans include, but are not limited to, dextran 70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation, Deerfield, Ill., U.S.A.).

Suitable thrombin antagonists include, but are not limited to, hirudin, bivalirudin, lepirudin, desirudin, argatroban, melagatran, ximelagatran and dabigatran. In one embodiment, the anticoagulant is argatroban. In another embodiment, the anticoagulant is argatroban at a final concentration of about 0.25-25 mg per unit of platelet. In another embodiment, the anticoagulant is argatroban at a final concentration of about 2.5 mg per unit of platelet.

The anticoagulants of the present invention also include factor Xa inhibitors, factor IIa inhibitors, and mixtures thereof. Various direct factor Xa inhibitors were synthesized and advanced to clinical development (Phase I-II) for the prevention and treatment of venous thromboembolic disorders and certain settings of arterial thrombosis [Hirsh and Weitz, Lancet, 93:203-241, (1999); Nagahara et al., Drugs of the Future, 20: 564-566, (1995); Pinto et al., 44: 566-578, (2001); Pruitt et al., Biorg. Med. Chem. Lett., 10: 685-689, (2000); Quan et al., J. Med. Chem. 42: 2752-2759, (1999); Sato et al., Eur. J. Pharmacol., 347: 231-236, (1998); Wong et al, J. Pharmacol. Exp. Therapy, 292:351-357, (2000)]. Factor IIa inhibitors include direct anti-IIa (thrombin) such as melagatran, the active form of pro-drug ximelagatran [Hirsh and Weitz, Lancet, 93:203-241, (1999); Fareed et al., Current Opinion in Cardiovascular, pulmonary and renal investigational drugs, 1:40-55, (1999)].

In certain embodiments, the anticoagulant is a short-to-ultra short acting anticoagulant. Short-to-ultra short acting means that the anticoagulant is cleared from circulation from 15 minutes to 8 hours, once the infusion of the anticoagulant into the patients is stopped. In one embodiment, the short-to-ultra short acting anticoagulant is a short-to-ultra short acting factor Xa inhibitor with a circulating half-life of less than 4 hours. Examples of ultra-short acting factor Xa inhibitors include, but are not limited to, DX-9065a, RPR-120844, BX-807834 and SEL series Xa inhibitors.

DX-9065a is a synthetic, non-peptide, propanoic acid derivative, 571 D selective factor Xa inhibitor (Dai chi). It directly inhibits factor Xa in a competitive manner with an inhibition constant in the nanomolar range [Herbert et al., J. Pharmacol. Exp. Ther. 276:1030-1038 (1996); Nagahara et al., Eur. J. Med. Chem. 30(suppl):140s-143s (1995)].

As a non-peptide, synthetic factor Xa inhibitor, RPR-120844 (Rhone-Poulenc Rorer), is one of a series of novel inhibitors which incorporate 3-(S)-amino-2-pyrrolidinone as a central template [Ewing et al., Drugs of Future 24(7):771-787 (1999)]. This compound has a Ki of 7 nM with selectivity >150-fold over thrombin, activated protein C, plasmin and t-PA. It prolongs the PT and αPTT in a concentration-dependent manner, being more sensitive to the αPTT. It is a fast binding, reversible and competitive inhibitor of factor Xa.

BX-807834 has a molecular weight of 527 Da and a Ki of 110 µM for factor Xa as compared to 180 µM for TAP and 40 nM for DX-9065a [Baum et al., Circulation. 98 (17), Suppl 1: 179, (1998)].

The SEL series of novel factor Xa inhibitors (SEL-1915, SEL-2219, SEL-2489, SEL-2711: Selectide) are pentapeptides based on L-amino acids produced by combinatorial chemistry. They are highly selective for factor Xa and potency in the pM range. The Ki for SEL 2711, one of the most potent analogues, is 0.003 M for factor Xa and 40 M for thrombin [Ostrem et al., Thromb. Haemost. 73:1306 (1995); Al-Obeidi and Ostrem., Exp. Opin. Ther. Patents 9(7):931-953 (1999)].

In another embodiment, the short-to-ultra short acting anticoagulant is a short-to-ultra short acting factor IIa inhibitor. Examples of short-to-ultra short acting anticoagulant include, but are not limited to, DUP714, hirulog, hirudin, melgatran and combinations thereof.

In certain embodiments, the platelet preservation solution further contains an effective amount of a pharmaceutically acceptable oxygen carrier. The oxygen carrier can be any suitable red blood cell substitute. Typically, the oxygen carrier is an acellular hemoglobin-based oxygen carrier substantially free of red cell membrane (stroma) contaminants. The term "pharmaceutically acceptable oxygen carrier" as used herein refers to a substance that has passed the FDA human safety trials at a hemoglobin dosage of 0.5 g/kg body weight or higher. An oxygen carrier suitable for the invention can be hemoglobin, ferroprotoporphyrin, perfluorochemicals (PFCs), and the like. The hemoglobin can be from human or any other suitable mammalian source. In one embodiment, the platelet preservation composition has a hemoglobin concentration from the range of 1 to 18 gm/dl and a methemoglobin concentration of less than about 5%. The hemoglobin based oxygen carrier will be chemically modified to mimic the oxygen loading and unloading characteristics of fresh red blood cells. Additionally, the chemical modification will enhance the buffering capacity of the preferred embodiment and preserve normal physiologic pH.

The platelet preservation composition of the present invention may further comprise a short-to-ultra-short acting broad spectrum anti-microbial agent. By short or ultra short acting anti-microbial agent is meant that the agent is cleared from circulation within 15 minutes to 8 hours after the infusion of the antimicrobial into the patient is stopped. Examples of such agents include, but are not limited to, Penicillin, Monobactam, Cephalosporin, Carbapenems, Vancomycin, Isoniazid, Ethambutol, Aminoglycoside, Tetracycline, Chloramphenicol, Macrolide, Rifamycin, Quinolone, Fluoroquinolone, Sulfonamide, Synergism, Polyene antibiotic, Imidazole, Triazole and Griseofulvin.

The platelet preservation composition can be used in any setting that requires the circulation of blood outside the body such as in patients undergoing open heart surgery, renal dialysis, plasmapheresis, and other procedures requiring platelet supplementation.

The platelet preservation composition can be directly added to a blood collection bag, or be kept in a separate bag and combined with the blood after collection. The blood in the collection bag optionally can be treated with an anticoagulant. In a typical setting, the preservative composition is added directly to the blood collection bag.

The platelet preservation composition of the present invention is used in an amount of about 60 to about 200 ml for about one unit of platelets (typically about 80 to about 100 ml of platelets). Alternatively, the preservative composition of the present invention is combined with about one unit of whole blood, typically about one pint, and separated into various components to afford about one-sixth to about one-tenth whole blood unit of treated platelets.

Storage of the Platelet Preparation

The preserved platelets can be stored at room temperature, at refrigeration temperatures (0° C.-12° C.) or at freezing temperatures (−80° C.-0° C.). In one embodiment, the platelets are stored at −20° C. to 12° C. In another embodiment, the platelets are stored at 0° C. to 12° C. In another embodiment, the platelets are stored at 4° C. to 12° C. In yet another embodiment, the platelets are stored at 4° C. to 8° C. In yet another embodiment, the platelets are stored at room temperature.

The platelets may be stored for a desired period of time. In certain embodiments, the desire period of time is one, two, three or four weeks.

Removal of the Antiplatelet Agent and the Anticoagulant

Prior to the clinical use of the preserved platelets, the antiplatelet agent and the anticoagulant in the preserved platelets are removed, thereby eliminating any concerns of adverse effects of the preservative agents. The use of short to ultra-short acting antiplatelet agent and anticoagulant also reduced the potential adverse effects of any leftover antiplatelet agent and anticoagulant in the preserved platelets. Any method that is capable of removing the antiplatelet agent and the anticoagulant while not damaging or activating the platelets can be used. Examples of the removal methods include, but are not limited to, filtration, affinity-based isolation, centrifugation and chromatography.

Filtration is a pressure driven separation process that uses membranes (or filters) to separate components in a liquid solution or suspension based on their size differences. Filtration can be broken down into two different operational modes-normal flow filtration (NFF) and tangential flow filtration (TFF). In NFF, fluid is connected directly toward the membrane under an applied pressure. Particulates that are too large to pass through the pores of the membrane accumulate at the membrane surface or in the depth of the filtration media, while smaller molecules pass through to the downstream side. This type of process is also called dead-end filtration.

In TFF, the fluid is pumped tangentially along the surface of the membrane. An applied pressure serves to force a portion of the fluid through the membrane to the filtrate side. As in NFF, particulates and macromolecules that are too large to pass through the membrane pores are retained on the upstream side. However, in this case the retained components do not build up at the surface of the membrane. Instead, they are swept along by the tangential flow. This feature of TFF makes it an ideal process for finer sized-based separations. TFF is also commonly called cross-flow filtration. However, the term "tangential" is descriptive of the direction of fluid flow relative to the membrane.

In one embodiment, the antiplatelet agents and anticoagulants are separated from the platelet preparation by diafiltration, wherein a diafiltration buffer is added to the platelet preparation during circulation to maintain a constant volume of the platelet preparation. Diafiltration is a TFF method of "washing" or removing permeable molecules (impurities, salts, solvents, small proteins, etc) from a solution. Because it is a significantly faster and scalable method, diafiltration frequently replaces membrane tube dialysis. The success of diafiltration is largely determined by the selection of an appropriate membrane. The membrane pores must be large enough to allow the permeable species to pass through and small enough to retain the larger species. A rule of thumb in selecting the membrane is to choose a membrane whose pore size is rated 2-5 times smaller than anything to be retained, and 2-5 times larger than anything to be removed by the filtration. A large variety of pore sizes are available in the ultrafiltration and micro filtration range for this purpose.

In one embodiment, an extraction liquid is circulated outside the filtering tube in a counter current manner to facilitate the filtration process. In a related embodiment, the extraction fluid comprises 0.9% w/v sodium chloride.

FIG. 1 shows a typical continuous diafiltration system in which the buffer is automatically added to the process reservoir by vacuum suction. It includes a pump (a), pressure measurement device (b), flow measurement device (c), process reservoir (d), buffer reservoir (e) and hollow fiber filter module (f). The pump circulates the process solution from the process reservoir, through the filter and back to the process vessel at a controlled flow and shear rate. Pressure measurements are acquired in this re-circulation loop to control and record the driving force through the membrane. Careful measurement of the permeate flow rate enables accurate process scale up and process optimization. Diafiltration occurs simply by adding the diafiltration buffer to this circulation loop. Working with a hollow fiber module, tubing and an air-tight sealable bottle is a simple means of performing a continuous diafiltration.

To begin the diafiltration in an airtight system, a vacuum needs to be created in the process vessel. This can be accomplished by submerging the buffer addition tube into a bottle of diafiltration buffer as shown in FIG. 1. As permeate flows out of the system, the vacuum in the sealed process reservoir pulls buffer into it at a flow rate equal to the process flux. When the target volume of diafiltration buffer has been collected in the permeate vessel, the process is stopped simply by stopping the permeate flow and breaking the vacuum seal on the feed reservoir.

When airtight systems are not possible, particularly for pilot and manufacturing scale processes, buffer addition can be controlled to match the permeate flow rate through the use of a single- or double-headed secondary pump adding buffer into the feed or process reservoir. Sometimes, it is advantageous to reduce the process volume by concentration before diafiltration. There is a relationship between the volume of buffer required to remove a permeable species and the product solution volume in the process reservoir. By understanding this relationship, the cost associated with the process time and the volume of buffer can be minimized.

In a preferred embodiment, the removal of antiplatelet agent and anticoagulants would involve the use of tangential flow filtration using micro filtration membranes. Microfiltration membrane materials include, but are not limited to, regenerated cellulose, cellulose acetate, polyamide, polyurethane, polypropylene, polysulfone, polyethersulfone, polycarbonate, nylon, polyimide and combinations thereof. In one embodiment, the microfiltration membrane is a hollow fiber membrane made of polysulfone or polyethersulfone. In another embodiment, the filter membrane tubes has inner diameter of 0.5 mm or greater with the membrane pore size of 0.05 micron or larger. In another embodiment, the membrane has a pore size ranging from a molecular weight cut off of 3000 daltons to 0.5 micron.

In other embodiments, these membranes can be chemically modified to provide a greater positive or negative charge depending on the specific application thereby selectively binding a solute of interest. Alternatively, the surface chemistry of these membranes can be modified to specifically bind solutes of interest such as the antiplatelet agents or direct thrombin inhibitors.

In another embodiment, the platelet preparation is passed through the hollow fiber membrane filter at flow rates ranging from 150 ml/minute to 370 ml/minute. Theses flow rates provide acceptable shear forces from 2000-s to 4000-s. An acceptable pump provides a wide range of flow rates and also provides continuous monitoring of inlet, retentate, permeate and transmembrane pressures. In one embodiment, the pump is the Kros Flow II pump (Spectrum Labs, Rancho Dominguez, Calif.). A replacement fluid suitable for the removal of antiplatelet and anticoagulant agents would be fluids that are used for the storage of platelets. Typically a 10 to 15 volume exchange will result in the removal of better than 99% of the added agents. Typically, 45 to 100 µg of antiplatelet agent, such as eftifibatide, and 2.5 to 10 mg of anticoagulant, such as argobatran, may be removed from a unit of platelet. Typically, unit of platelets obtained by the buffy coat method would contain $3\times10^{11}$ platelets in approximately 300 ml of plasma or other suitable preservation solution. A unit platelets collected by aphaeresis usually contain $5\times10^9$ platelets in 250 ml of plasma or other suitable fluid.

In another embodiment, the platelet preparation is passed through the hollow fiber filter in a diafiltration device at flow rates ranging from 20 to 400 ml/min, preferably 150 to 400 ml/min. The hollow fiber membrane filters with a pore size ranging from molecular weight cut off of 3000 daltons to 0.5 micron are acceptable. The preferred pore size is 0.05 micron. For the exchange of one unit of platelets (300 to 400 ml) the preferred surface area of the filtration module is 2500 $cm^2$. This setting allows the complete removal (>99%) of the antiplatelet and anticoagulant agents contained in a unit of platelets in 15 minutes with a flow rate of 370 ml/min. The diafiltration buffer (i.e., replacement fluid) can be any solution suitable for platelet storage. In one embodiment, the diafiltration buffer is a commercially available platelet storage solution (T-Sol) with 20% plasma.

In affinity-based isolation, the antiplatelet agent and anticoagulant are removed from a platelet preparation by passing the platelet preparation through the surface of a material that binds specifically to the antiplatelet agent and anticoagulant. The affinity can be based on biological interactions such as antibody-antigen interaction and ligand-receptor interaction, chemical interaction such as hydrophilicity or hydrophobicity based interaction, and electrical interaction such as charge-based interactions. Methods of affinity based-isolation are well known in the art. In one embodiment, the antiplatelet agent and anticoagulant are removed from a platelet preparation using magnetic beads that specifically bind to the antiplatelet agent and anticoagulant.

In one embodiment, the antiplatelet agent and anticoagulant are removed from a platelet preparation by passing the platelet preparation through a porous material that specifically binds to the antiplatelet agent and the anticoagulant.

In certain embodiments, the porous material comprises a nanofiber. Examples of nanofiber include, but are not limited to, cellulose nanofibers, biodegradable nanofibers and carbon nanofibers.

Cellulose nanofibers may be obtained from various sources such as flax bast fibers, hemp fibers, kraft pulp, and rutabaga, by chemical treatments followed by innovative mechanical techniques. The nanofibers thus obtained have diameters between 5 and 60 nm. The ultrastructure of cellulose nanofibers is investigated by atomic force microscopy and transmission electron microscopy. The cellulose nanofibers are also characterized in terms of crystallinity. In one embodiment, the membrane filter is a reinforced composite film comprising 90% polyvinyl alcohol and 10% nanofibers.

The chemistry of these cellulose fibers can be modified to provide specific binding sites for a given antiplatelet agent and/or an anticoagulant. These fibers can be coated onto the surface of currently available disposable filter platforms like those used for sterilizing small volumes of fluids.

Biodegradable polymers, such as poly(glycolic acid) (PGA), poly(L-lactic acid) (PLLA) and poly(lactic-co-glycolic acid) (PLGA), can be dissolved individually in the proper solvents and then subjected to electrospinning process to make nanofibrous scaffolds. Their surfaces can then be chemically modified using oxygen plasma treatment and in situ grafting of hydrophilic acrylic acid (AA). In one embodiment, the biodegradable nanofibrous scaffold has a fiber thickness in the range of 200-800 nm, a pore size in the range of 2-30 micron, and porosity in the range of 94-96%.

The ultimate tensile strength of PGA will be about 2.5 MPa on average and that of PLGA and PLLA will be less than 2 MPa. The elongation-at-break will be 100-130% for the three nanofibrous scaffolds. When the surface properties of AA-grafted scaffolds are examined, higher ratios of oxygen to carbon, lower contact angles and the presence of carboxylic (—COOH) groups are identified. With the use of plasma treatment and AA grafting, the hydrophilic functional groups can be successfully adapted on the surface of electrospun nanofibrous scaffolds. These surface-modified scaffolds provide the necessary sites for adding ligands specific to the binding of a given antiplatelet agent and anticoagulant.

There are several approaches that can be utilized to convert activated carbon into bioreactive fibers. An example is provided to demonstrate the ability of these modified carbon nanofibers to provide carboxylic, hydroxyl and other chemically reactive sites for the binding of any ligand of interest.

Carbon nanofibers (CNF) can be synthesized by chemical vapor deposition (CVD). Amino acids, such as alanine, aspartic acid, glutamic acid and enzymes such as glucose oxidase (GOx) can be adsorbed on CNF. The properties of CNF (hydrophilic or hydrophobic) are characterized by the pH value, the concentration of acidic/basic sites and by naphthalene adsorption. These fibers are readily amenable to crosslinking with ligands f interest, i.e., the ability to selectively bind to antiplatelet agents and anticoagulants.

The antiplatelet agent and anticoagulant may also be removed from a platelet preparation by centrifugation or chromatography. Briefly, platelets may be precipitated under conditions that do not precipitate the antiplatelet agent and anticoagulant. The precipitated platelets are then washed and resuspended for clinical use. Similarly, chromatographic methods such as column chromatography may also be used to separate the platelets from the antiplatelet agent and anticoagulant. Alternatively, the antiplatelet agent and anticoagulant may be removed from a platelet preparation by affinity-based removal methods such as magnetic beads coated with antibodies that bind to the antiplatelet agent and/or anticoagulant.

Another aspect of the present invention relates to a platelet preservation solution that contains eptifibitide in the range of about 5-500 µg/unit of platelet, and argatroban in the range of about 0.25-25 mg/unit of platelet, an isotonic buffer solution, and 20-30% (v/v) plasma. In one embodiment, the isotonic buffer solution is the InterSol® solution (Fenwal, Inc., Lake Zurich, Ill.).

The present invention is further illustrated by the following examples which should not be construed as limiting. The contents of all references, patents and published patent applications cited throughout this application, as well as the Figures and Tables are incorporated herein by reference.

EXAMPLES

Example 1

Removal of Integrilin Using Diafiltration

A standard UV absorbance curve at 214 nm with Integrilin concentrations ranging from 3 to 50 µg/ml was established based on the following measurements:

| Integrilin Concentration | O.D 214 |
|---|---|
| 50 µg/ml | 0.710 |
| 25 µg/ml | 0.532 |
| 12.5 µg/ml | 0.299 |
| 6.25 µg/ml | 0.126 |
| 3.125 µg/ml | 0.015 |

A test fluid containing 50 µg/ml Integrilin was circulated through a hollow fiber filter (Spectrum Laboratories X20S-300-02S) at a circulation rate of 100 ml/min. Briefly, the test fluid was placed in an air tight container with a starting OD214 of 0.710. As the test fluid circulated through the hollow fiber filter, the retentate volume decreased. The lost fluid volume was replaced with fresh fluid from a second container. After about a 10 minute circulation and a six volume exchange, the OD214 of the test fluid was less than 0.01.

Example 2

Removal of Inhibitors from Platelet Concentrate

Figure 2:
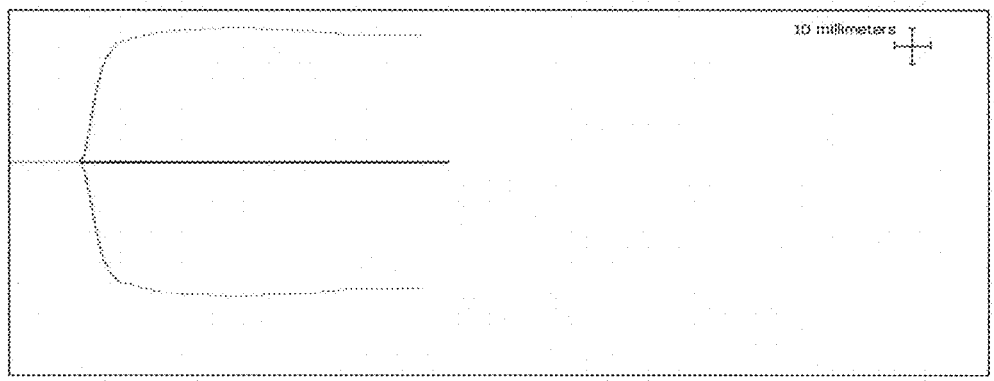
FIG. 2 is a thromboelastogram (TEG) of platelets with inhibitors before (black tracing) and after plasma filtration (green tracing).
Figure 3:
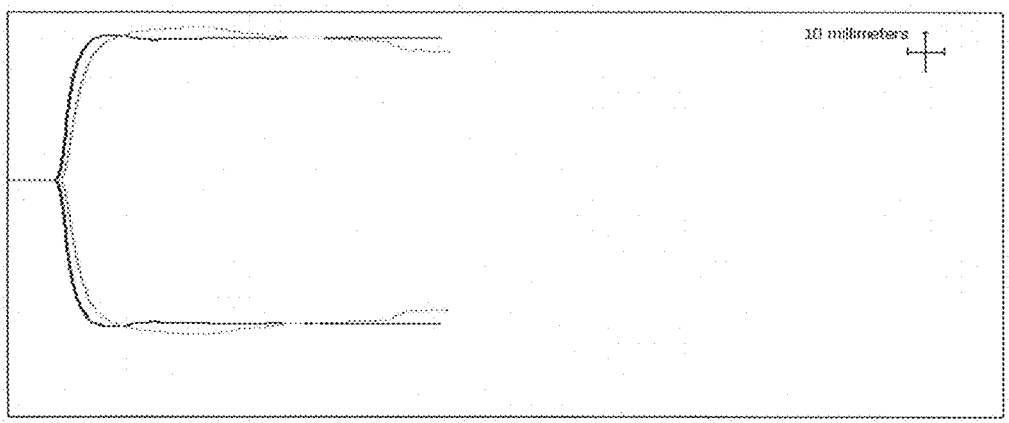
FIG. 3 is a TEG of platelets with saline before (black tracing) and after plasma filtration (green tracing).
Figure 4:
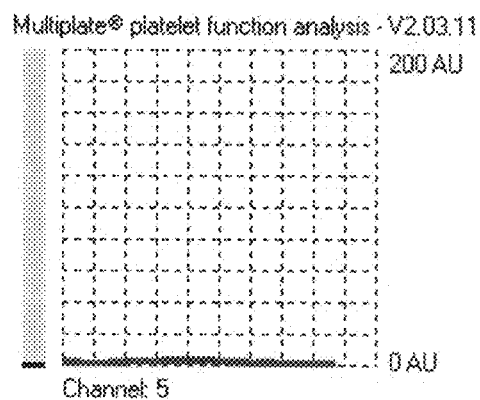
FIG. 4 is a diagram showing the platelet response to thrombin related activated peptide (TRAP) in the presence of the inhibitors.

In one experiment, platelet concentrates obtained by the buffy coat method were used for the study. 48 micrograms of Integrilin (Eptifibatide), a GPIIb/IIIa inhibitor and 2.4 mg of Argabotran, a synthetic thrombin inhibitor, were added to 350 ml of platelets. Removal of the inhibitors was initiated by diafiltration. 15 ml of the platelet concentrate was diafiltered against 60 ml of a solution containing 20% fresh frozen plasma in a commercially used platelet storage solution (T-Sol). The samples were stored overnight and platelet functionality was measured on Day 2, by TEG and using standard agonists such as TRAP and collagen. FIG. 2 shows the TEG scan of the test sample before (black tracing) and after diafiltration (green tracing). FIG. 3 shows the TEG scan of a control sample (platelets with saline) before (black tracing) and after diafiltration (green tracing). The result in FIG. 3 suggests that most inhibitors had been removed by diafiltration. FIG. 4 shows the response to TRAP in the presence of the inhibitors.

Figure 5:
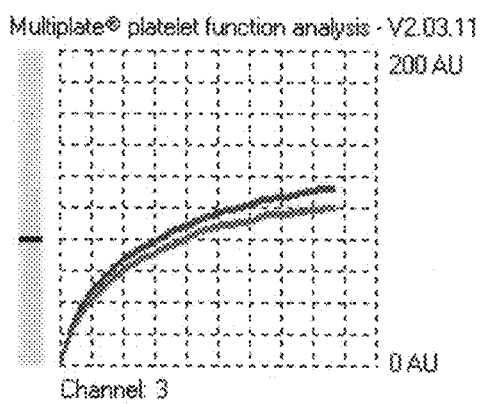
FIG. 5 is a diagram showing the platelet response to TRAP after the removal of the inhibitors.
Figure 6:
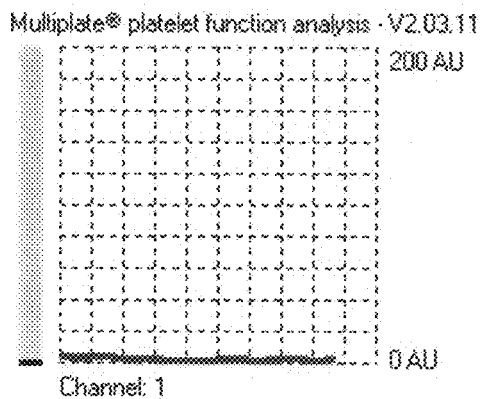
FIG. 6 is a diagram showing the platelet response to collagen in the presence of the inhibitors.
Figure 7:
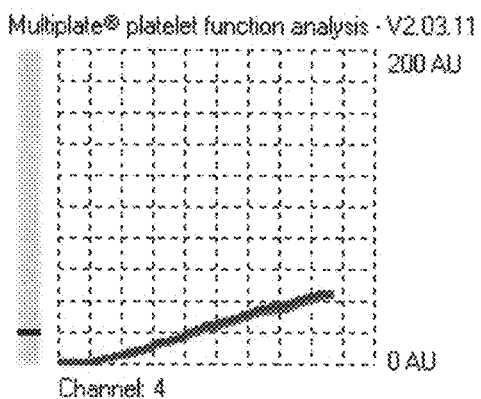
FIG. 7 is a diagram showing the platelet response to collagen after the diafiltration

FIG. 5 shows the response to TRAP after the removal of the inhibitors. FIG. 6 shows the response to collagen in the presence of the inhibitors and finally FIG. 7 shows the response to Collagen after the diafiltration.

In another experiment, Integrilin and Argabotran were added to platelet units at three times the therapeutic concentrations (i.e., 48 micrograms for Integrilin and 2.4 mg for argatroban in 350 ml of platelets). Prior to the addition of the inhibitors, baseline data of platelet functionality was obtained. These baseline data included TEG, which assesses overall platelet function and clot strength, as well as the TRAP test and the collagen test, which are additional markers of platelet functionality.

Figure 8:
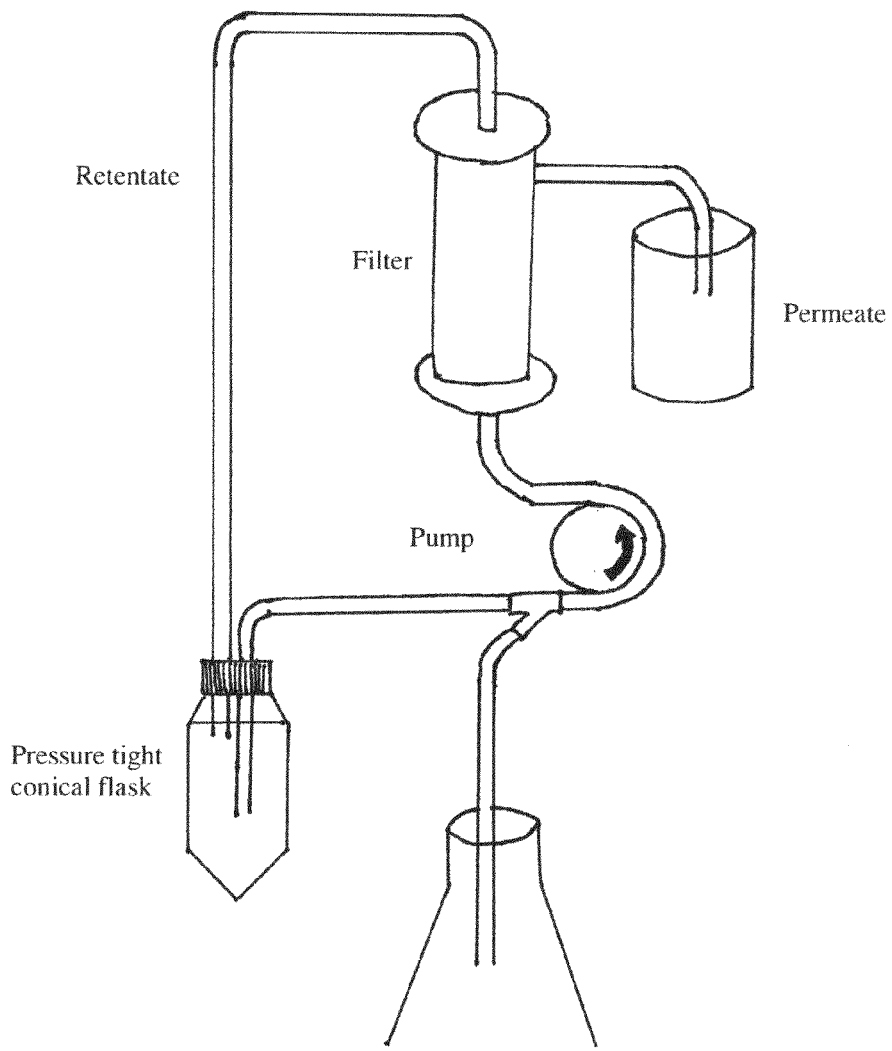
FIG. 8 is a diagram showing an experimental platelet filtration system.

The diafiltration was conducted in 40 ml aliquots using an airtight 50 ml conical flask, a polysulfone hollow fiber cross flow module with a surface area of 240 $cm^2$ (FIG. 8). A sequential exchange with increasing volumes of standard platelet additive solution (InterSol®), indicated that a 15 volume exchange provided optimum results with the inhibitors. The pore size of the hollow fiber membrane selected was 0.05 micron. The pore size can range from 3000 daltons molecular weight cut off to 0.5 micron. The 15 volume exchange can be conducted with any currently available additive solution used for storing platelets.

Following the 15 volume exchange, homologous fresh frozen plasma was added to the platelets to achieve a plasma concentration of 25% (v/v). This is required because the plasma provides the soluble components of coagulation, thereby permitting the functionality tests performed.

The recirculation rate of the platelets (in Intersol containing 30% plasma) was set at 370 ml/minute. This was calculated to create a shear force of approximately 4000-s. This shear force has been shown not to activate platelets.

The inlet pressure over three experiments was 8.13 psi, the retentate pressure was 6.15 psi. The pressure differential was 2 psi. The permeate pressure was essentially 0 and the transmembrane pressure was 7.15 psi. These pressures remained very constant throughout the exchange, indicating no fouling of the membrane. The permeate flow rate was around 26 ml/minute.

Figure 9:
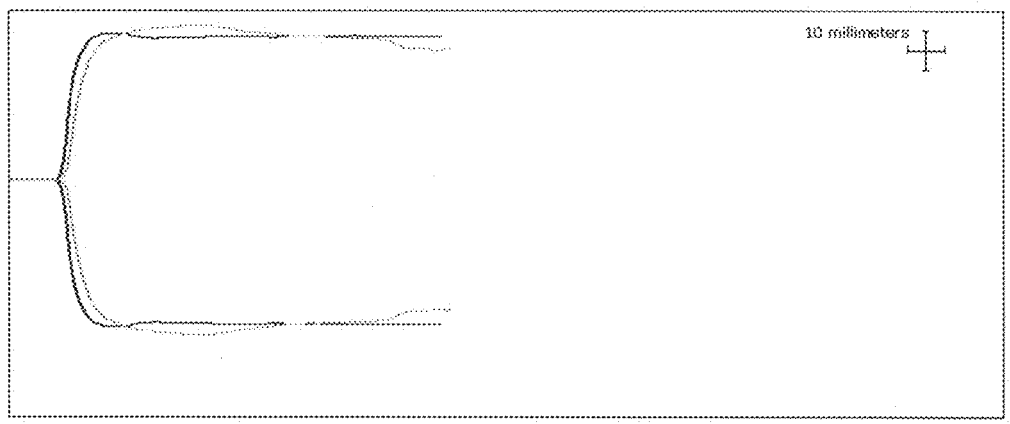
FIG. 9 is a TEG showing (black tracing) platelets without inhibitors and platelets after the antiplatelet agents had been removed with 15 volume exchange (green tracing).

When argatroban is present, it completely blocks the activation of platelets and results in a straight line on the TEG. FIG. 9 shows the thromboelastograms of platelets without the inhibitors. The R value, i.e., the time it takes before the clot starts to form, as indicated by the splitting of the line, averaged 10.7 minutes. Following the 15 volume exchange, the average R value was 10.75. In a total of 4 experiments conducted, the R value after 15 volume exchange was equal to or less than the baseline R value. Based on the thromboelastogram, at least a 99.99% removal of inhibitors was achieved.

The maximum amplitude, MA, was unchanged from baseline, when the slight dilution of the platelets during the 15 volume exchange is taken into consideration. This parameter reflects the removal of Integrilin.

Figure 10:
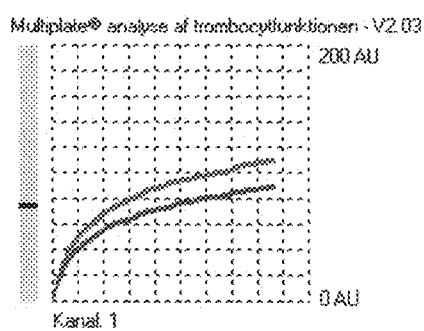
FIG. 10 is a diagram showing the platelet response to TRAP in the absence of the inhibitors.
Figure 11:
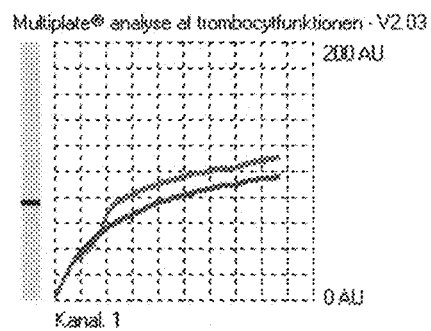
FIG. 11 is a diagram showing the platelet response to TRAP after the removal of inhibitor by 15 volume exchange with InterSol®.

FIG. 10 shows the results of the TRAP assay run on the platelets prior to the addition of the inhibitors. The area under the curve is expressed as standardized units. The control had a value of 67. The same assay run on the platelets after 15 volume exchange with InterSol® was 68 (FIG. 11). This assay is more sensitive to the presence of Integrilin. It therefore indicates essentially complete removal of this inhibitor.

Figure 12:
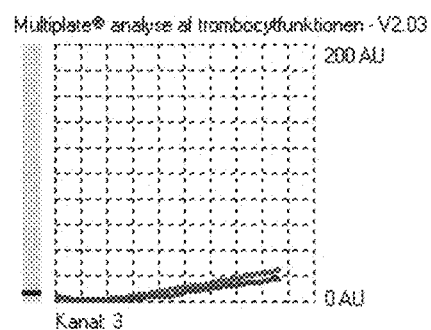
FIG. 12 is a diagram showing the platelet response to collagen in the absence of the inhibitors.
Figure 13:
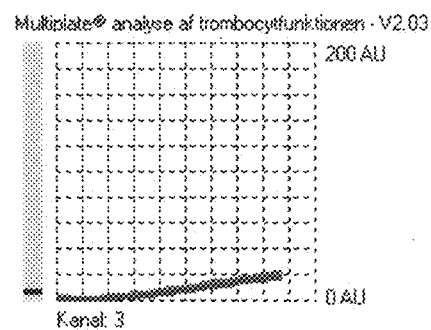
FIG. 13 is a diagram showing the platelet response to collagen after the removal of inhibitor by 15 volume exchange with InterSol®.

The functionality of the platelets was also tested using collagen as the activator. The baseline value for the platelets was 6 (FIG. 12). The value obtained for the platelets following the removal of the inhibitors with 15 volume exchange with InterSol® was also 6 (FIG. 13).

The experiment described above is a method by which complete replacement of plasma in platelet concentrates, whether collected by apheresis, buffy coat or any other method, can be readily accomplished.

Example 3

Preserving Platelets Using the Platelet Preservation Composition

In order to determine the effectiveness of the platelet preservative composition of the present invention, the following experiments were conducted: Platelets were collected by the buffy coat method according to standard Blood Bank procedure. Platelet concentrates (PCs) thus obtained were split into two units. The first split unit (control sample) was stored in a control solution (Intersol® platelet additive solution from Fenwal Inc., Lake Zurich, Ill.) containing approximately 30% plasma. The second split unit (test sample) was stored in a test platelet preservation solution (InterSol® solution containing approximately 30% plasma, eptifibitide at 50 μg/unit of platelet, and argatroban at 2.5 mg/unit of platelet), which is referred to hereinafter as "the Biovec preservation solution."

On Day 2 and Day 7, the standard quality control (QC) test was performed. Additionally, platelet functionality tests were conducted by TEG and with the Multiplate Analyzer. The former measures clot strength (MA) and reaction time, and is an indicator of the platelet response to activation in the presence of kaolin. The latter measures the platelets response to agonists such as collagen and TRAP.

During the testing period, the oxygenation, pH, glucose consumption and lactate production of the control sample and test sample were well within the acceptable limits.

Figure 14:
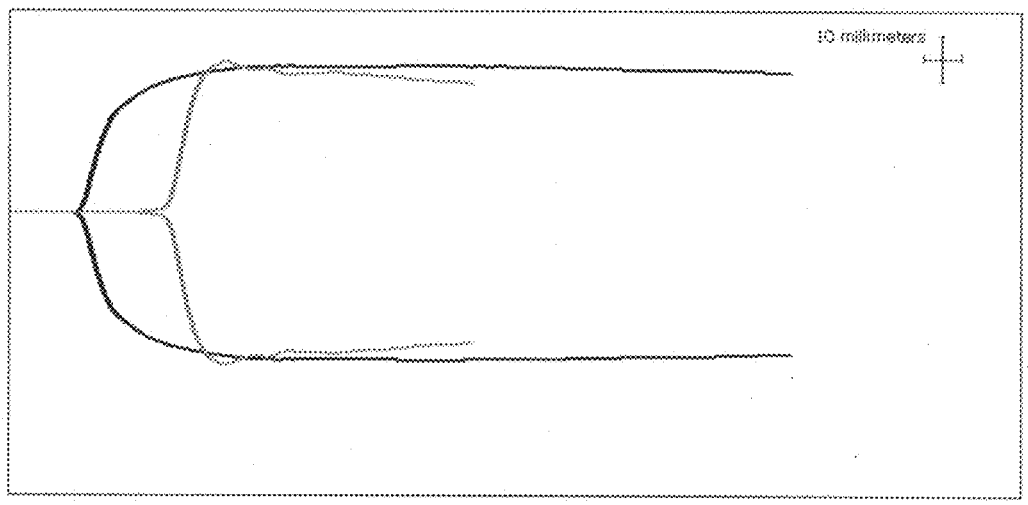
FIG. 14 is a diagram showing TEG tracings of platelets stored under current methods (black tracing) compared with platelets stored with the preservative of the present invention (green tracing).
Figure 15:
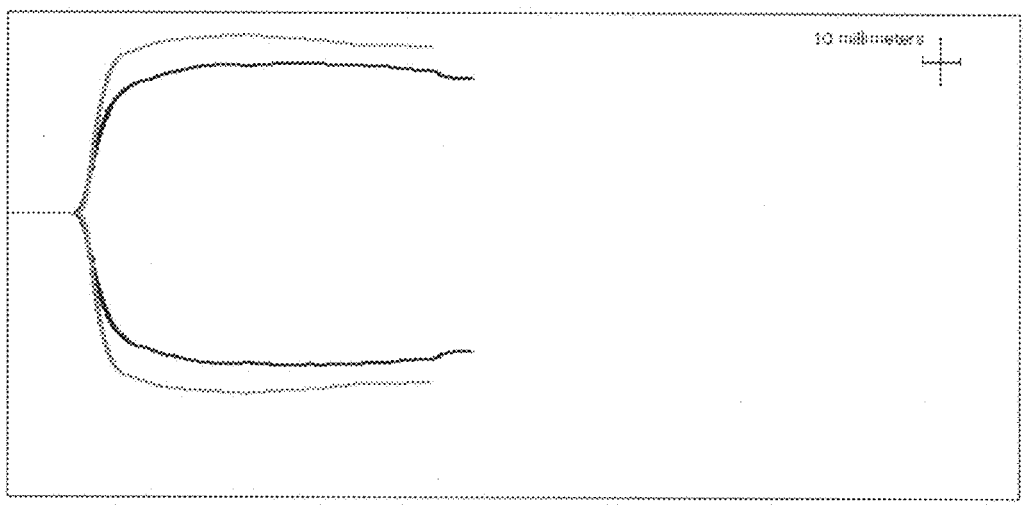
FIG. 15 is a diagram showing TEG tracings of platelets following one day of storage of a second set of split platelet concentrate units. The control is again represented by the black tracing and the test unit by the green tracing.

On Day 2, all functionality tests were comparable between the control and test samples. Results from the two samples are shown in FIGS. 14 and 15. FIG. 14 shows TEG tracings of platelets stored under current methods (black tracing) compared with platelets stored with the Biovec preservative (green tracing). The data was obtained following one day of storage. There is essentially no difference in the ability of either platelet concentrate to form a strong clot. The reaction time R of the test sample was 50% longer than that of the control sample. This is a reflection of the presence of residual inhibitors in the test sample. The residual inhibitor concentration has been determined to be less than 5% of starting concentration. FIG. 15 shows data following one day of storage of a second set of split platelet concentrate units. The control is again represented by the black tracing and the Biovec test unit by the green tracing. In this instance there has been complete removal of the platelet inhibitors. Furthermore, platelets stored with the Biovec preservation solution demonstrate a stronger clot than the control. This suggests that the inhibitors affect both the reaction time as well as the clot strength.

Diafiltration

The inhibitors were removed by a four volume exchange against Intersol containing approximately 20% fresh frozen plasma This was accomplished by using a hollow fiber filter (X20S~300-0.2N from Spectrum Labs, Rancho Dominguez, Calif.). The exchange was carried out prior to the testing of the samples.

Figure 16:
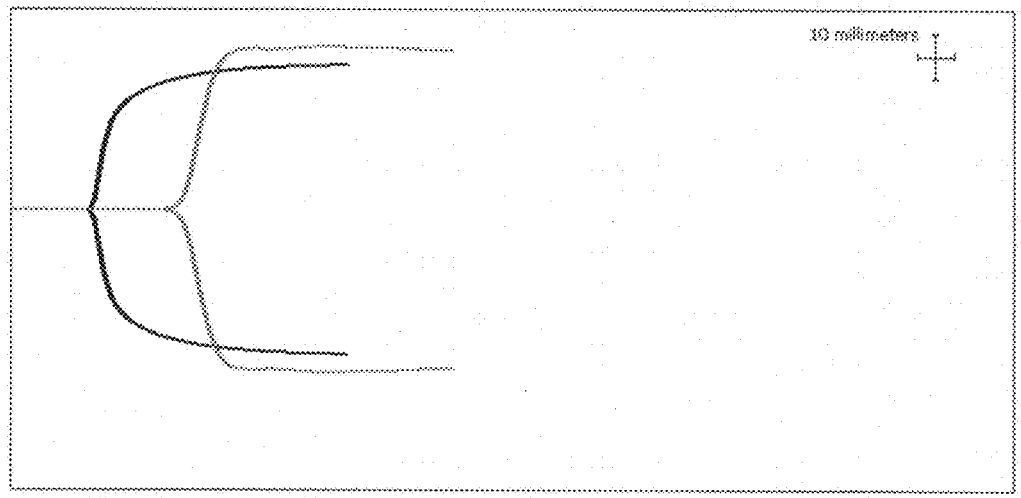
FIG. 16 is a diagram showing TEGs of the same units shown in FIG. 14 but after 7 days of storage following standard Blood Bank practices.
Figure 17:
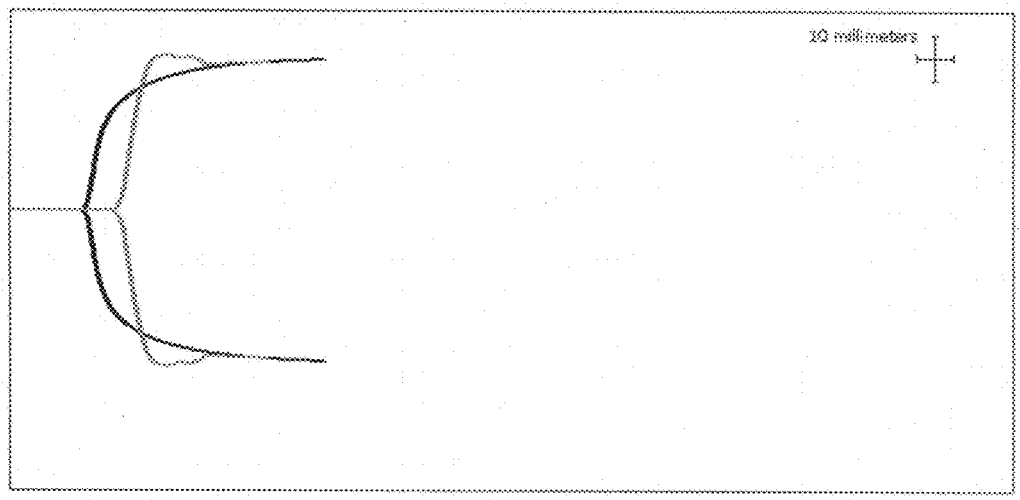
FIG. 17 is a diagram showing TEGs of the same units shown in FIG. 15 but after storage for 7 days.

On Day 7, the MA or clot strength on the TEG indicates that the control sample formed a significantly weaker clot compared to the test sample. This finding was further confirmed with the Multiplate analyzer. As shown in FIGS. 16 and 17, the test sample showed clear response to agonists (similar to the response at Day 2), whereas the control sample showed minimal to no response. Specifically, FIG. 16 shows thromboelastograms of the same units shown in FIG. 14, but after 7 days of storage following standard Blood Bank practices. It shows that despite the residual presence of the inhibitors, platelets stored with the Biovec preservative demonstrate a greater ability to form a strong clot when activated than the platelet stored with the current methods. FIG. 17 shows thromboelastograms of the same units shown in FIG. 15, but after storage for 7 days. Once again, the split unit stored in the Biovec preservative (green) shows a greater ability to respond to agonist (kaolin) than the control unit.

These results indicate that platelet stored in Biovec preservative solution was able to respond to stimulus significantly better than platelets preserved in currently available solutions. This finding is confirmed by the platelet responses to TRAP and collagen (FIGS. 18-33).

Figure 18:
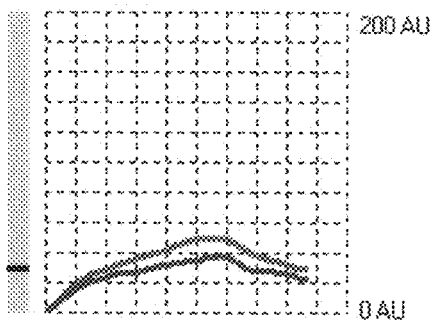
FIG. 18 is a diagram showing response of platelets stored in the Biovec preservative solution to TRAP test using the multiplate analyzer. This was measured after one day of storage under standard blood bank procedures.

FIG. 18 shows response of platelets stored in the Biovec preservative, to thrombin related activated peptide (TRAP) test using the multiplate analyzer. This was measured after one day of storage under standard blood bank procedures.

Figure 19:
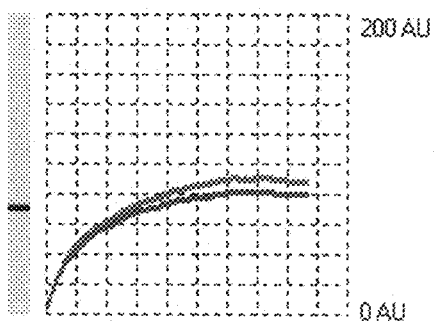
FIG. 19 is a diagram showing response of the split control unit to the TRAP test. This measurement was also made after one day of storage.

FIG. 19 shows response of the split control unit to the TRAP test. This measurement was also made after one day of storage.

Figure 20:
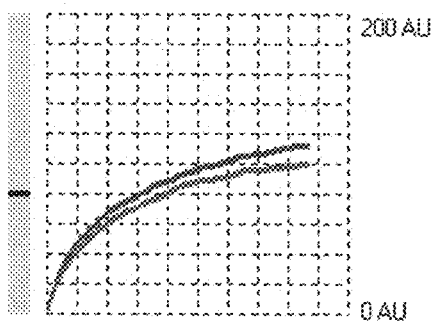
FIG. 20 is a diagram showing response to TRAP of a second split platelet unit stored in the Biovec preservative solution.

FIG. 20 shows response to TRAP of a second split platelet unit stored in the Biovec preservative solution.

Figure 21:
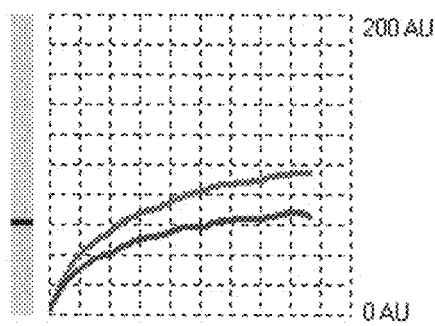
FIG. 21 is a diagram showing response to TRAP of the matched split platelet unit stored with the currently available preservative solution.

FIG. 21 shows response to TRAP of the matched split platelet unit stored with the currently available preservative solution.

Figure 22:
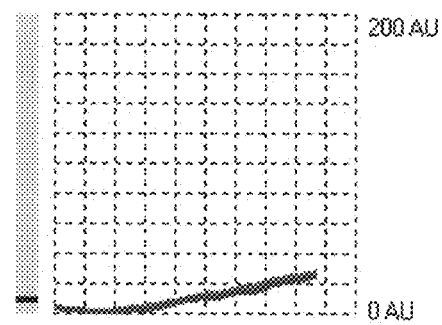
FIG. 22 is a diagram showing response to collagen of platelets stored for one day in the Biovec preservative solution.

FIG. 22 shows response to collagen as agonist, of platelets stored for one day in the Biovec preservative solution.

Figure 23:
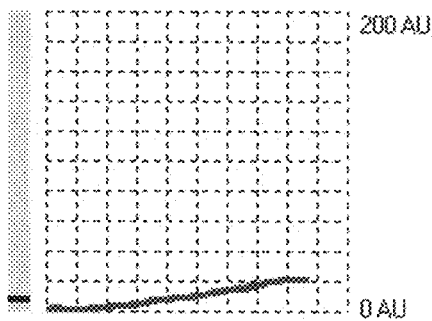
FIG. 23 is a diagram showing response to collagen of the matched split control unit stored in currently available medium.

FIG. 23 shows response to collagen of the matched split control unit stored in currently available medium.

Figure 24:
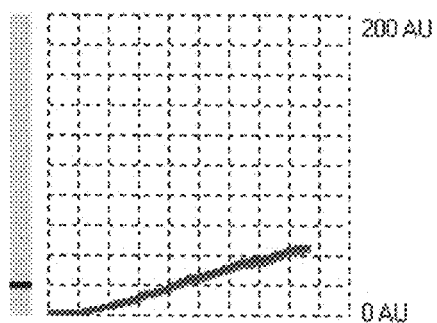
FIG. 24 is a diagram showing response to collagen of the second test platelet unit after one day of storage in the Biovec preservative solution.

FIG. 24 shows response to collagen of the second test platelet unit after one day of storage in the Biovec preservative solution.

Figure 25:
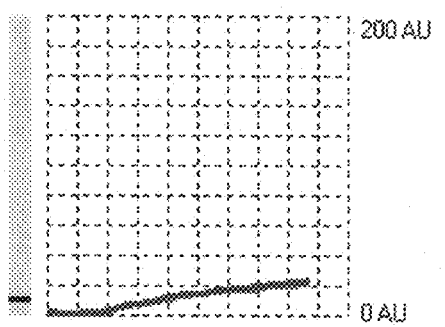
FIG. 25 is a diagram showing response to collagen of the matched split control platelet unit after one day of storage.

FIG. 25 shows response to collagen of the matched split control platelet unit after one day of storage.

Figure 26:
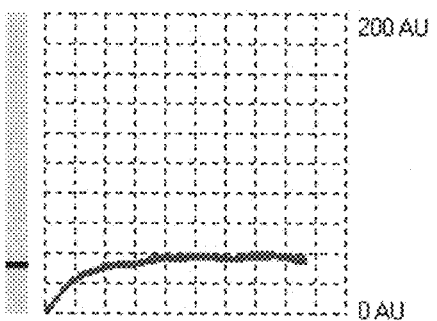
FIG. 26 is a diagram showing response to the TRAP test of the platelet unit stored in the Biovec preservative solution after 7 days of storage.

FIG. 26 shows response to the TRAP test of the platelet unit stored in the Biovec preservative solution after 7 days of storage. This test unit had an identical response to TRAP on one day after storage.

Figure 27:
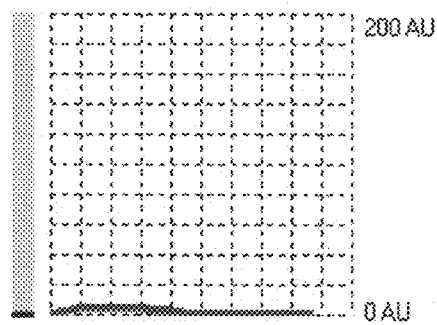
FIG. 27 is a diagram showing response to the TRAP test of the matched split control platelet unit after 7 days of storage under standard Blood Bank conditions.

FIG. 27 shows response to the TRAP test of the matched split control platelet unit after 7 days of storage under standard Blood Bank conditions. Compared to its response one day after storage (63 AU), there was no response to the same agonist.

Figure 28:
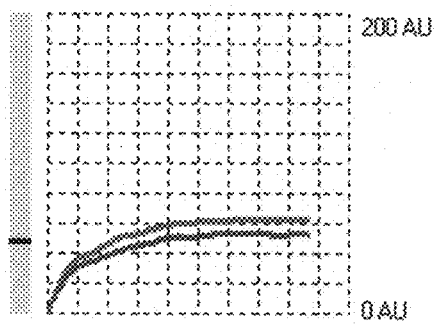
FIG. 28 is a diagram showing response to the TRAP test of the second platelet unit stored in the Biovec preservative solution. Once again, its response was essentially unchanged from its response one day after storage.

FIG. 28 shows response to the TRAP test of the second platelet unit stored in the Biovec preservative solution. Once again, its response was essentially unchanged from its response one day after storage.

Figure 29:
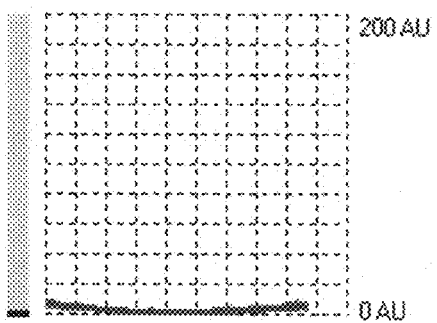
FIG. 29 is a diagram showing response to the TRAP test of the matched control platelet unit stored in the currently available preservative solution.

FIG. 29 shows response to the TRAP test of the matched control platelet unit stored in the currently available preservative solution. There is no response to the agonist.

Figure 30:
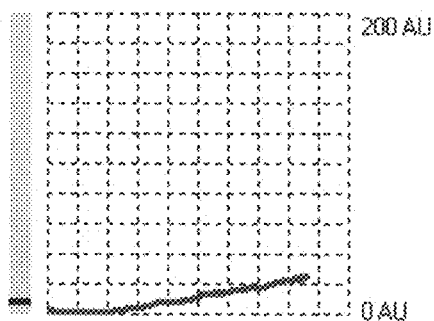
FIG. 30 is a diagram showing response to collagen of the split platelet unit stored in the Biovec preservative solution.

FIG. 30 shows response to collagen of the split platelet unit stored in the Biovec preservative solution. Once again, the response after 7 days of storage appears to be essentially unchanged from its response one day after storage.

Figure 31:
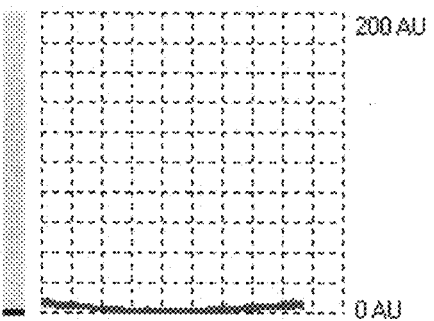
FIG. 31 is a diagram showing response to the collagen test of the matched control split platelet unit.

FIG. 31 shows response to the collagen test of the matched control split platelet unit Once again platelets stored with currently available preservative solution are unresponsive to agonists after 7 days in storage.

Figure 32:
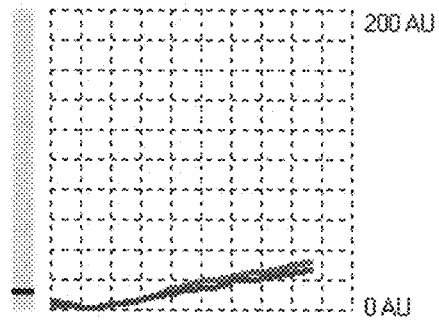
FIG. 32 is a diagram showing response to the collagen test of the second split platelet unit stored in the Biovec preservative solution.

FIG. 32 shows response to the collagen test of the second split platelet unit stored in the Biovec preservation solution. Here again, little difference is noted from the response observed after one day of storage.

Figure 33:
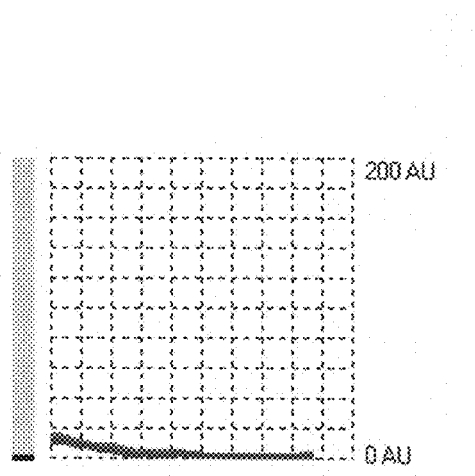
FIG. 33 is a diagram showing response to the collagen test of the matched split platelet unit stored in the currently available preservative solution.

FIG. 33 shows response to the collagen test of the matched split platelet unit stored in the currently available preservative solution. Just like the other control unit, there is no response to the agonist after 7 days of storage.

Taken together, the data presented clearly demonstrates that platelets stored in the Biovec preservative solution (1) formed a stronger clot even in the presence of some leftover inhibitors from the Biovec preservative, both after one day of storage and following 7 days of storage, which is a clear reflection of better maintenance of platelet intra cellular structure and metabolism and (2) showed a strong response to commonly used agonists such as TRAP and collagen.

In sharp contrast, platelets stored in one of the commonly used preservative solution had no response to the same agonists.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims, The claims are intended to cover the claimed components and steps in any sequence which is effective to meet the objectives there intended, unless the context specifically indicates the contrary.

What is claimed is:

1. A method for preserving platelets, comprising:
mixing platelets with a platelet preservation composition to form a platelet preparation, said platelet preservation composition comprises an effective amount of a short-to-ultra short acting antiplatelet agent comprising a short-to-ultrashort GPIIb/IIIa inhibitor, and an effective amount of a short-to-ultra short acting anticoagulant comprising a short-to-ultrashort acting factor Xa inhibitor;
storing the platelet preparation for a desired period of time; and
removing the antiplatelet agent and the anticoagulant from the platelet preparation by diafiltration prior to transfusion of the platelets.

2. The method of claim 1, wherein said removing step comprises:
flowing the platelet preparation through a filtering tube comprising a filtering membrane and separating the antiplatelet agent and anticoagulant from the platelet preparation by tangential flow filtration.

3. The method of claim 2, wherein the filter membrane comprises a material selected from the group consisting of regenerated cellulose, cellulose acetate, polyamide, polysulfone, polyethersulfone and combinations thereof.

4. The method of claim 3, wherein the filter membrane comprises polysulfone or polyethersulfone.

5. The method of claim 4, wherein the filter membrane has a pore size ranging from molecular weight cut off of 3000 daltons to 0.5 micron.

6. The method of claim 2, wherein the filtering tube has an inner diameter of at least 0.5 mm.

7. The method of claim 2, wherein the platelet preparation flows through the filtering tube at a flow rate of 150 to 3500 ml/min.

8. The method of claim 2, wherein an extraction liquid is circulated outside the filtering tube in a counter current manner.

9. The method of claim 8, wherein the extraction fluid comprises 0.9% w/v sodium chloride.

10. The method of claim 1, wherein the antiplatelet agent is eptifibatide and wherein the anticoagulant is argatroban.

11. The method of claim 10, wherein the antiplatelet agent is eptifibatide at a final concentration of 50 µg/unit of platelet, wherein the anticoagulant is argatroban at a final concentration of 2.5 mg/unit of platelet and wherein said unit comprises between $5 \times 10^9$ to $3 \times 10^{11}$ platelets.

* * * * *